(12) United States Patent
Cohen

(10) Patent No.: US 6,206,882 B1
(45) Date of Patent: Mar. 27, 2001

(54) PLATING SYSTEM FOR THE SPINE

(75) Inventor: Herb Cohen, Shelton, CT (US)

(73) Assignee: Surgical Dynamics Inc., Norwalk, CT (US)

( * ) Notice: Subject to any disclaimer, the term of this patent is extended or adjusted under 35 U.S.C. 154(b) by 0 days.

(21) Appl. No.: 09/537,207

(22) Filed: Mar. 29, 2000

Related U.S. Application Data

(60) Provisional application No. 60/126,995, filed on Mar. 30, 1999.

(51) Int. Cl.[7] ............................................. A61B 17/80
(52) U.S. Cl. ................................................ 606/69
(58) Field of Search ................. 606/69, 70, 71

(56) References Cited

U.S. PATENT DOCUMENTS

| | | |
|---|---|---|
| 3,741,205 | 6/1973 | Markolf et al. . |
| 4,388,921 | 6/1983 | Sutter et al. . |
| 4,503,848 | 3/1985 | Caspar et al. . |
| 4,611,581 | 9/1986 | Steffee . |
| 4,696,290 | 9/1987 | Steffee . |
| 4,790,297 | 12/1988 | Luque . |
| 4,836,196 | 6/1989 | Park et al. . |
| 4,957,497 | 9/1990 | Hoogland et al. . |
| 5,085,660 | 2/1992 | Lin . |
| 5,147,361 | 9/1992 | Ojima et al. . |
| 5,201,737 * | 4/1993 | Leibinger et al. ................ 606/69 |
| 5,209,751 | 5/1993 | Farris et al. . |
| 5,261,910 | 11/1993 | Warden et al. . |
| 5,324,290 | 6/1994 | Zdeblick et al. . |
| 5,344,421 | 9/1994 | Crook . |
| 5,346,492 * | 9/1994 | Morgan ............................. 606/69 |
| 5,364,399 | 11/1994 | Lowery et al. . |
| 5,486,176 | 1/1996 | Hildebrand et al. . |
| 5,601,553 | 2/1997 | Trebing et al. . |
| 5,730,743 * | 3/1998 | Kirsch et al. ..................... 606/69 |
| 5,743,913 * | 4/1998 | Wellisz .............................. 606/69 |
| 5,766,175 * | 6/1998 | Martinotti ......................... 606/69 |

* cited by examiner

Primary Examiner—Paul J. Hirsch

(57) ABSTRACT

A spinal fixation plate is disclosed which includes an elongated plate body having a central longitudinal axis, opposed top and bottom surfaces and an outer periphery, the outer periphery of the plate body is defined in part by opposed first and second lateral edges. A plurality of flexure slots extend inwardly from the first lateral edge perpendicular to the longitudinal axis of the plate body, and a plurality of flexure slots extend inwardly from the second lateral edge perpendicular to the longitudinal axis of the plate body. The flexure slots terminate at locations axially spaced from one another relative to the longitudinal axis of the plate body.

27 Claims, 4 Drawing Sheets

PLATING SYSTEM FOR THE SPINE

CROSS-REFERENCE TO RELATED APPLICATIONS

The subject application claims priority to U.S. Provisional Patent Application Ser. No. 60/126,995 filed Mar. 30, 1999, the disclosure of which is herein incorporated by reference in its entirety.

BACKGROUND OF THE DISCLOSURE

1. Field of the Disclosure

The subject disclosure relates to implantable spinal stabilization systems for surgical treatment of spinal disorders, and more particularly, to a plating system for use in the treatment of the lumbar and thoracic spine.

2. Background of the Related Art

The spinal column is a complex system of bones and connective tissue which protects critical elements of the nervous system. Despite these complexities, the spine is a highly flexible structure, capable of a high degree of curvature and twist through a wide range of motion. Trauma or developmental irregularities can result is spinal pathologies which limit this range of motion.

The use of fixation plates for the treatment of spinal disorders has grown considerably over the years. Fixation plates are commonly employed to maintain spinal elements such as vertebrae in a desired spatial relationship to aid in healing or the correction of a spinal disorder. Examples of prior art spinal fixation plates are disclosed in U.S. Pat. No. 4,696,290 to Steffee; U.S. Pat. No. 5,209,751 to Farris et al.; U.S. Pat. No. 5,261,910 to Warden et al.; U.S. Pat. No. 5,486,176 to Hildebrandt et al.; and U.S. Pat. No. 5,601,553 to Trebling et al.

In general, prior art fixation plates such as these, have a rigid inflexible construction which is difficult to conform to the anterior surfaces of the vertebrae which form the spinal column. Thus, it is often necessary for a surgeon to bend or contort a plate to conform to the anterior surfaces of the vertebrae during a surgical procedure. This adds to the duration and complexity of the procedure.

It would be desirable to provide a spinal fixation plate that has a higher degree of flexibility than spinal fixation plates found in the prior art, so as to enable a surgeon to easily conform the plate to the anterior surfaces of the spinal vertebrae during a surgical procedure, thereby reducing the duration and complexity of the procedure.

SUMMARY OF THE DISCLOSURE

The subject disclosure is directed to a unique plating system for anterior fixation on the lumbar and thoracic vertebrae of the spine. In accordance with a preferred embodiment of the subject disclosure, the plating system includes an elongated bone plate having a central longitudinal axis and a predetermined thickness. The bone plate is defined by opposed first and second end portions, opposed top and bottom surfaces and an outer periphery. The outer periphery of the bone plate is defined in part by opposed first and second lateral edges. At least one flexure slot extends inwardly from the first lateral edge of the bone plate, and at least one flexure slot extends inwardly from the second lateral edge of the bone plate. The flexure slots terminate at locations spaced from one another, such as, for example, substantially along the longitudinal axis of the bone plate.

Preferably, each flexure slot extends perpendicular to the longitudinal axis of the bone plate. However, a bone plate is disclosed wherein each flexure slot extends at an acute angle with respect to the longitudinal axis of the bone plate. Those skilled in the art will readily appreciate that the angle of the flexure slots could vary depending upon the desired characteristics of the bone plate. For example, bone plates mat be provided wherein the flexure slots extend at 30° angles, 45° angles, or 60° angles.

The number of flexure slots provided in the bone plate can also vary in accordance with the subject disclosure. In one preferred embodiment of the subject disclosure, at least three flexure slots extend inwardly from the first lateral edge of the bone plate, and at least three flexure slots extend inwardly from the second lateral edge of the bone plate. Preferably, each flexure slot extends through the entire thickness of the bone plate from the top surface thereof to the bottom surface thereof, and terminates in a rounded surface configured to reduce stress concentrations. Each flexure slot preferably has a substantially similar length with respect to the longitudinal axis of the bone plate. However, a bone plate is disclosed wherein the flexure slots are of varying length with respect to the longitudinal axis of the bone plate so as to achieve a desired degree of elasticity.

In accordance with the subject disclosure, each end portion of the bone plate has at least one bore extending therethrough for receiving a bone fastener configured to secure the bone plate to vertebrae along the length of the spine. In accordance with the subject disclosure a bone screw is secured within a bore of the bone plate in one of two ways. A bone screw may be secured within the bore of the plate by a threaded locking nut or by compressible locking washer. Preferably, each bore is countersunk so as to cooperate with either a locking nut or a locking washer.

These and other unique features of the plating system disclosed herein and the method of installing the same will become more readily apparent from the following description of the drawings.

BRIEF DESCRIPTION OF THE DRAWINGS

So that those having ordinary skill in the art to which the disclosed apparatus appertains will more readily understand how to construct and use the same, reference may be had to the drawings wherein.

These and other features of the plating system disclosed herein and the manner in which it is deployed will become more readily apparent to those having ordinary skill in the art from the following detailed description of the invention taken in conjunction with the drawings.

DETAILED DESCRIPTION OF THE PREFERRED EMBODIMENTS

Figure 1:
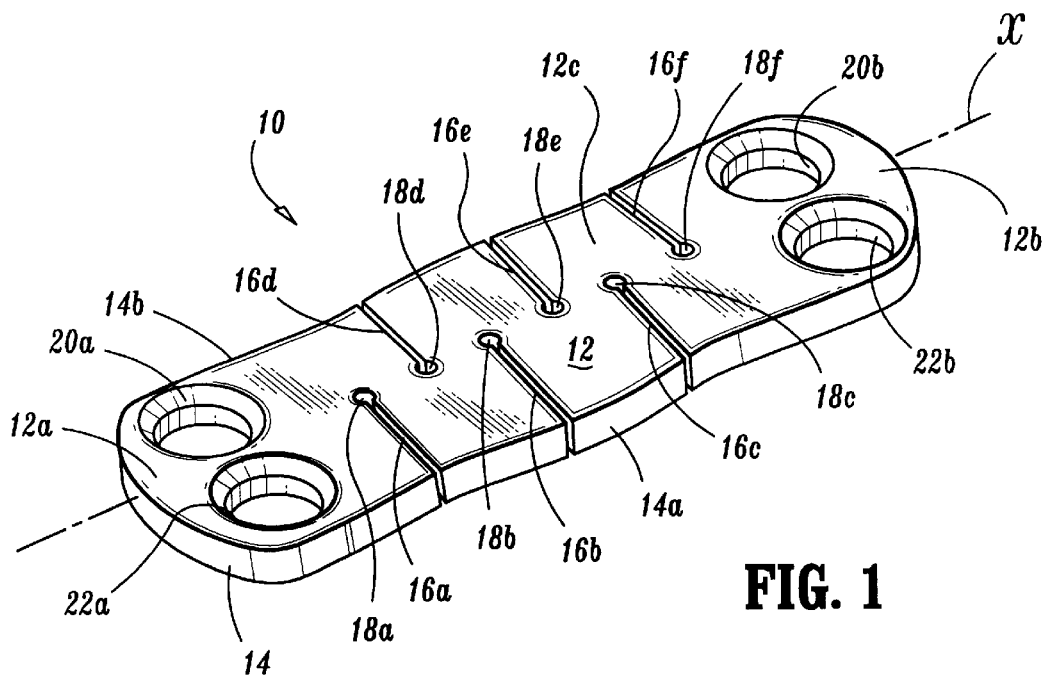
FIG. 1 is a perspective view of a flexible bone plate constructed in accordance with a preferred embodiment of the subject disclosure wherein a plurality of flexure slots are provided to increase the flexibility of the bone plate.

Referring now to the drawings wherein like reference numerals identify similar structural elements of the spinal plating system disclosed herein, there is illustrated in FIG. 1 a bone plate constructed in accordance with a preferred embodiment of the subject disclosure and designated generally by reference numeral 10. Bone plate 10 is adapted and configured for anterior fixation to the lumbar and thoracic vertebrae during a surgical procedure.

Figure 2:
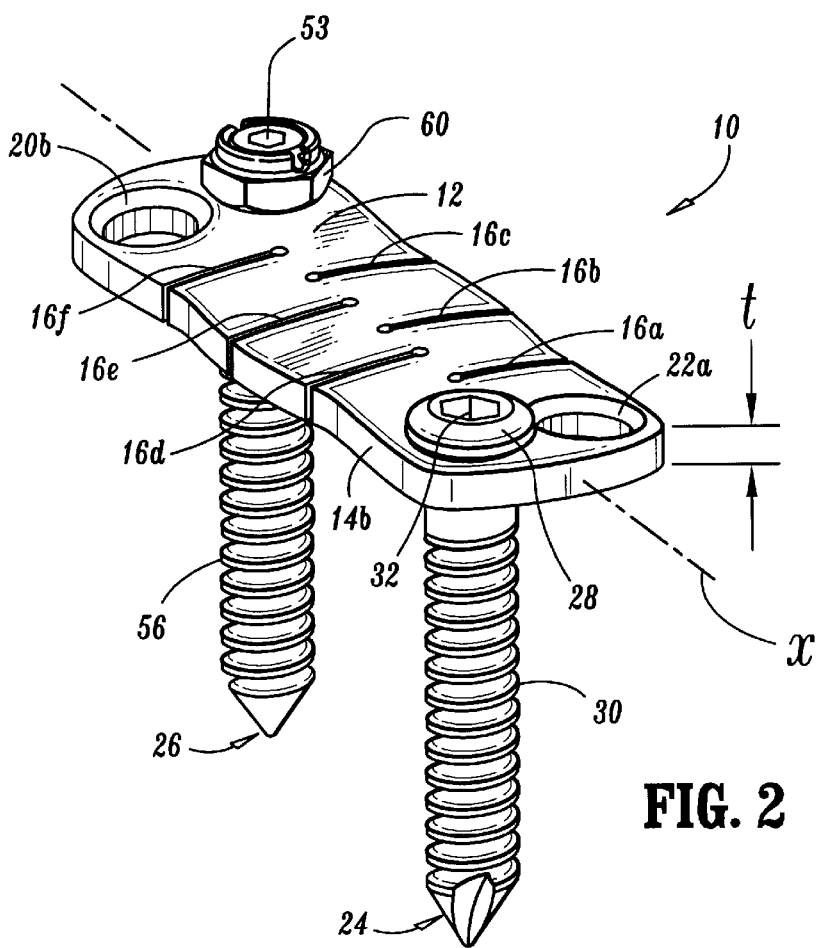
FIG. 2 is a perspective view of the flexible bone plate of FIG. 1 with a pair of bone screws engaged within reception bores of the bone plate, wherein one bone screw is secured to the bone plate with a compressible locking washer and the other bone screw is secured to the bone plate with a threaded locking nut.

Referring to FIGS. 1 and 2, bone plate 10 is defined by a substantially planar elongated plate body 12 having a central longitudinal axis "x" and a predetermined thickness "t". Plate body 12 is preferably made of a high-strength, lightweight, biocompatible material such as, for example, stainless steel or titanium. It includes opposed end portions 12a and 12b and central body portion 12c with opposed top and bottom surfaces and an outer periphery 14. As shown, the outer periphery 14 of plate body 12 has a curved contour which is designed to aid in the manipulation of the device during a surgical procedure. Those skilled in the art to which the subject disclosure appertains will readily appreciate however, that the outer periphery of the bone plate need not be curved and may otherwise have generally planar peripheral surfaces or a textured peripheral surface.

In accordance with the subject disclosure, the plate body 12 of bone plate 10 is provided with a plurality of transverse flexure slots which enhance the elasticity or flexibility of the device during a surgical procedure. This characteristic enables a surgeon to easily conform the plate body to the contours of the spinal vertebrae without the need for extraneous surgical instrumentation. In particular, referring to FIGS. 1 and 2, three transverse flexure slots 16a–16c extend inwardly from the first lateral edge 14a of plate body 12, and three flexure slots 16d–16f extend inwardly from the second lateral edge 14b of plate body 12. Each flexure slot 16a–16f preferably extends through the entire thickness "t" of the plate body 12 from the top surface thereof to the bottom surface thereof.

Flexure slots 16a–16f terminate at locations spaced from one another, preferably substantially along the central longitudinal axis "x" of the plate body 12. The termination point of each flexure slot is preferably approximately located on or adjacent to the central longitudinal axis "x" of the plate body 12. The flexure slots 16a–16f terminate in rounded surface area 18a–18f, respectively. The curved surface areas are configured to reduce stress concentrations and thus prevent stress fractures in the plate body when the plate undergoes flexure.

While plate body 12 is shown and described herein as having three spaced apart transverse flexure slots on either side of the central longitudinal axis "x" of the plate body 12, the number of flexure slots can vary depending upon the desired degree of flexibility of the device. Indeed, it is possible to provide only one flexure slot on each side of the central longitudinal axis of the plate body if only a minor degree of flexibility is desired. The position of such transverse flexure slots with respect to one another could also vary depending upon the desired flexure characteristics. Furthermore, as described hereinbelow with respect to FIGS. 7 and 8, the size and angular orientation of the flexure slots with respect to the central longitudinal axis of the bone plate can differ so as to vary the flexure characteristics of the bone plate.

With continuing reference to FIGS. 1 and 2, a first pair of counter-sunk bores 20a, 22a extends through the first end portion 12a of plate body 12, and a second pair of counter-sunk bores 20b, 22b extends through the second end portion 12b of plate body 12. The paired bores 20a, 22a and 20b, 22b are adapted and configured to receive and engage threaded bone screws, such as, for example, either one of the bone screws 24 or 26 illustrated in FIG. 2. (Both types of screws are shown with plate 10 in FIGS. 2–4 for convenience) Those skilled in the art will readily appreciate that the number of screw bores provided in the opposed end portions of the bone plate can vary from a few as one to as many four depending upon the degree to which it is desired to fasten the bone plate to the spine, which may be a function of the location of the bone plate along the spinal column.

Figure 3:
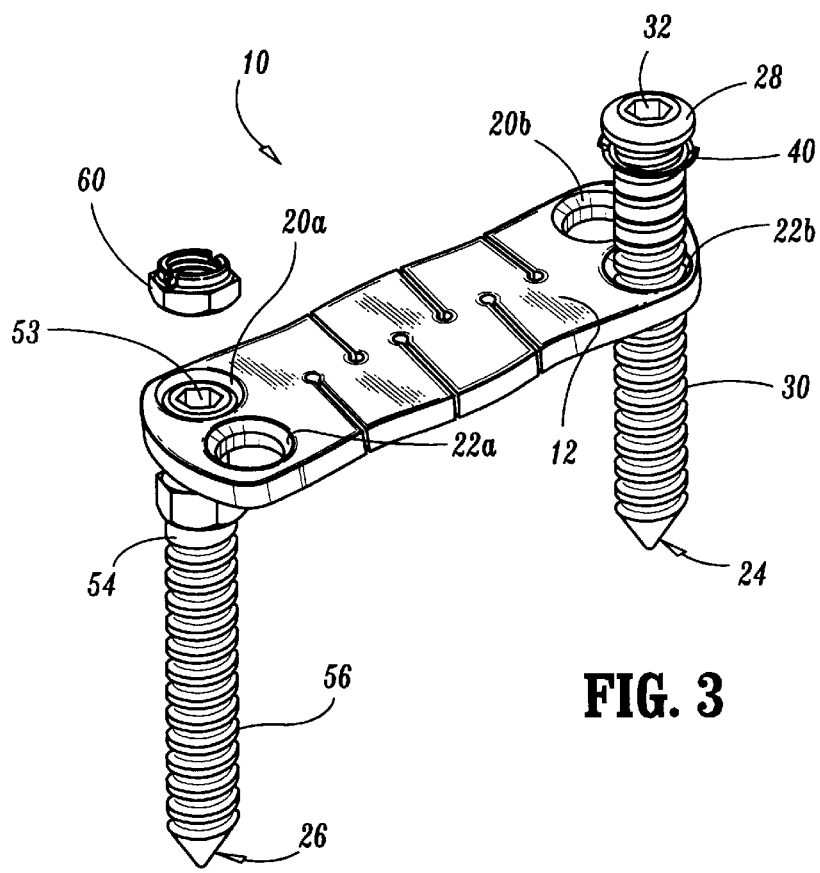
FIG. 3 is a perspective view of the flexible bone plate of FIG. 1, illustrating a step in the engagement of a bone screw with the bone plate.
Figure 4:
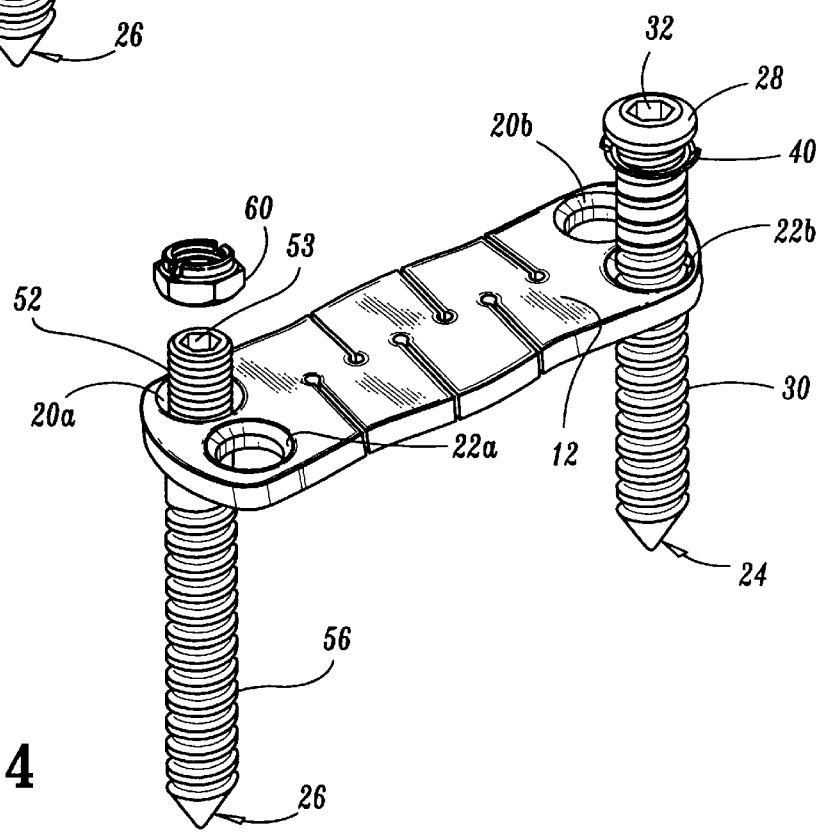
FIG. 4 is a perspective view of the flexible bone plate of FIG. 1, illustrating another step in the engagement of a bone screw with the bone plate.
Figure 6:
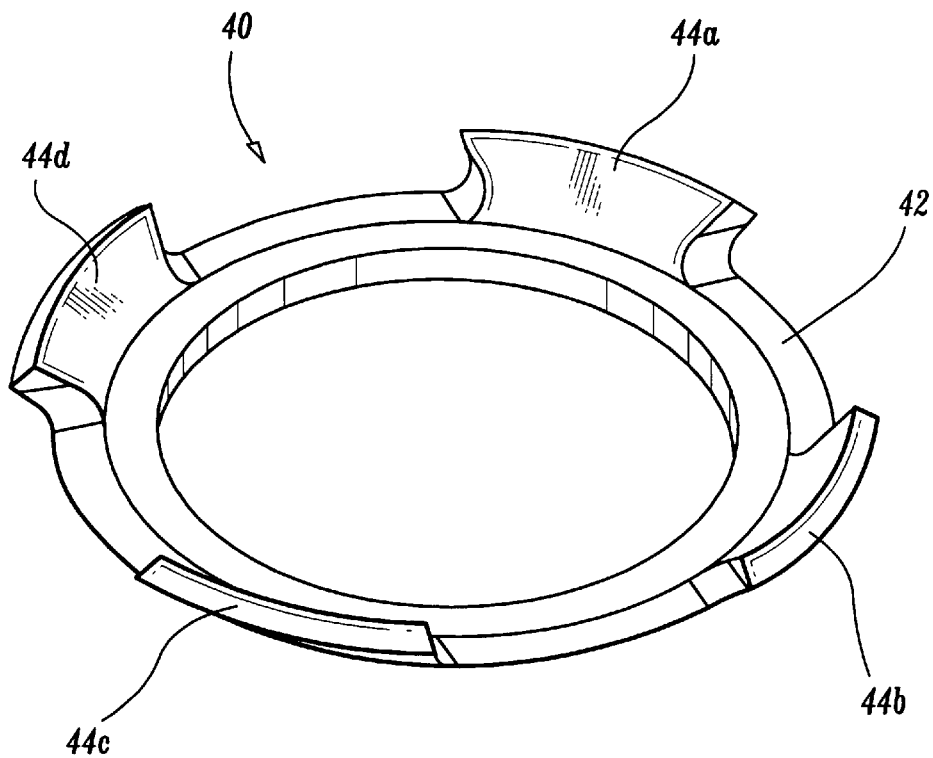
FIG. 6 is a perspective view of the compressible locking washer used in conjunction with the bone screw illustrated in FIG. 2.

Bone screw 24 includes an enlarged head 28 and a threaded shaft 30 which depends from the head. Head 28 has a hexagonal port 32 for receiving the working end of a surgical tool (not shown), and threaded shaft 30 has a helical thread formation that is particularly adapted to fixedly secure screw 24 to bone. As illustrated in FIGS. 3 and 4, bone screw 24 cooperates with a compressible lock washer 40 that is adapted and configured to securely engage bone screw 24 within a countersunk bore of plate body 12. In particular, as best seen in FIG. 6, lock washer 40 includes an annular base portion 42 from which depends four circumferentially spaced apart engagement tabs 44a–44d that are adapted and configured to bite into and engage the under-surface of the head 28 of bone screw 24 and the countersunk surface of a bore, as the lock washer 40 is compressed against the countersunk bore surface, so as to advantageously prevent movement of the bone screw within the countersunk bore.

Figure 5:
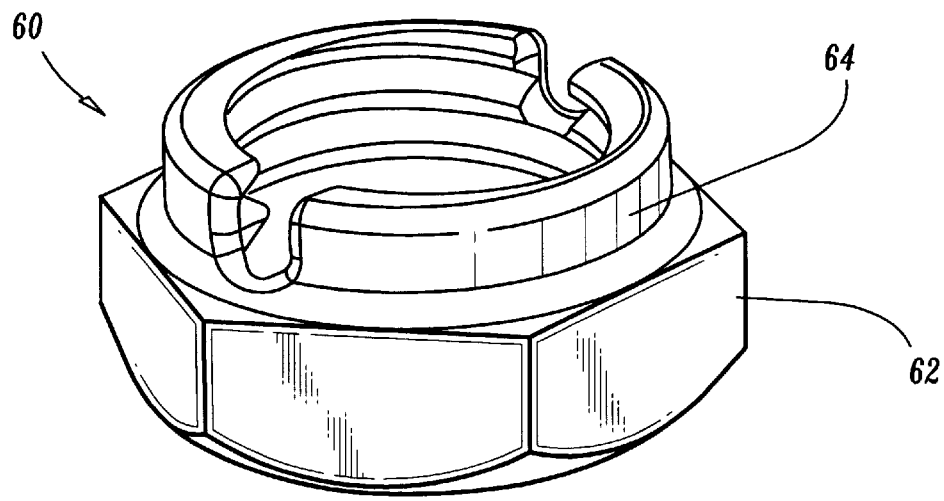
FIG. 5 is a perspective view of the threaded locking nut used in conjunction with the bone screw illustrated in FIG. 2.

With continuing reference to FIGS. 2 through 4, bone screw 26 includes an elongated body having a threaded upper body portion 52 with a hexagonal tool port 53, a medial shank portion 54 and a threaded shaft portion 56. The threaded shaft portion 56 includes a helical thread formation adapted to fixedly secure screw 26 to bone. The medial shank portion 54 separates the shaft portion 56 from the upper body portion 52. The upper body portion 52 includes a conventional thread formation adapted to support a threaded support nut 58 and a threaded lock nut 60. As best seen in FIG. 5, lock nut 60 includes a hexagonal body portion 62 from which depends a reduced diameter locking flange 64 adapted to engage the thread formation of the upper body portion during assembly.

Figure 7:
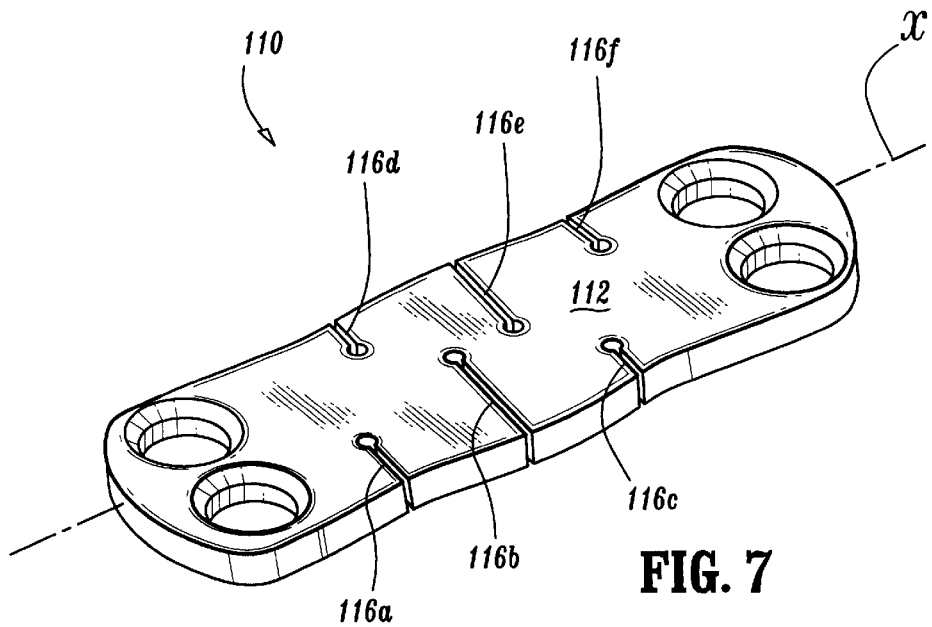
FIG. 7 is a perspective view of another flexible bone plate constructed in accordance with a preferred embodiment of the subject disclosure wherein the bone plate includes flexure slots of differing length.

Referring to FIG. 7, there is illustrated another bone plate constructed in accordance with a preferred embodiment of the subject disclosure designated generally by reference numeral 110. Bone plate 110 is substantially similar to bone plate 110 in that the plate body 112 is provided with a set of spaced apart flexure slots 116a–116f that extend inwardly from both of the opposed lateral edges of the plate body. However, the flexure slots 116a–116f of plate body 112 differ form those of plate body 12 in that flexure slots 116a–116f are of differing length with respect to the central longitudinal axis "x" of plate body 112. For example, flexure slots 116a and 116c are shorter that flexure slot 116b. Similarly, flexure slot 116e is longer than flexure slots 116d and 116f. The slot configuration of bone plate 110 produces different flexibility characteristics than the slot configuration of bone plate 10.

Figure 8:
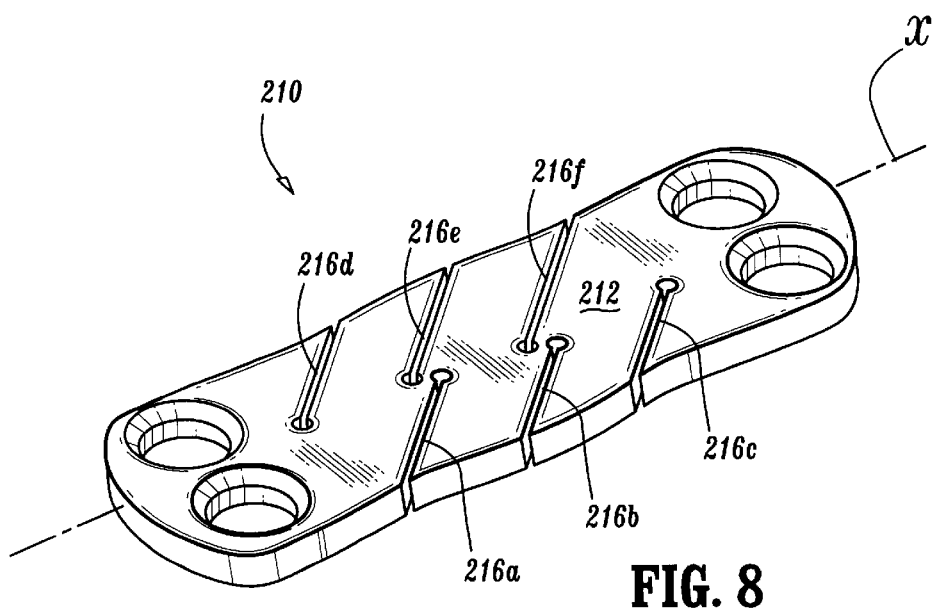
FIG. 8 is a perspective view of yet another flexible bone plate constructed in accordance with a preferred embodiment of the subject disclosure wherein the bone plate includes flexure slots oriented at acute angles to the central longitudinal axis of the bone plate.

Referring to FIG. 8, there is illustrated another bone plate constructed in accordance with a preferred embodiment of the subject disclosure designated generally by reference numeral 210. Bone plate 210 includes a set of spaced apart flexure slots 216a–216f that extend inwardly from both of the opposed lateral edges of the plate body and are oriented at an acute angle with respect to the central longitudinal axis of the plate body 212. The angle of orientation of flexure slots 216a–216f with respect to the central longitudinal axis "x" of plate body 212 can vary within the range of 0° to 90° depending upon the desired flexibility characteristics of the bone plate.

Although the apparatus disclosed herein has been described with respect to preferred embodiments, it is apparent that modifications and changes can be made thereto without departing from the spirit and scope of the invention as defined by the claims.

What is claimed is:

1. A spinal fixation system comprising:
    an elongated bone plate having a central longitudinal axis and a predetermined thickness, the bone plate defined by opposed first and second end portions, opposed top and bottom surfaces and an outer periphery, the outer periphery of the bone plate defined in part by opposed first and second lateral edges, at least one flexure slot extending inwardly from the first lateral edge of the bone plate, at least one flexure slot extending inwardly from the second lateral edge of the bone plate, the flexure slots terminating at locations spaced from one another, and each end portion of the bone plate having at least one bore extending therethrough for receiving a bone fastener.

2. A spinal fixation system as recited in claim 1, wherein each flexure slot extends perpendicular to the longitudinal axis of the bone plate.

3. A spinal fixation system as recited in claim 1, wherein each flexure slot extends at an acute angle with respect to the longitudinal axis of the bone plate.

4. A spinal fixation system as recited in claim 1, wherein at least three flexure slots extend inwardly from the first lateral edge of the bone plate, and at least three flexure slots extend inwardly from the second lateral edge of the bone plate.

5. A spinal fixation system as recited in claim 1, wherein each flexure slot extends through the thickness of the bone plate from the top surface thereof to the bottom surface thereof.

6. A spinal fixation system as recited in claim 1, wherein each flexure slot terminates at a location adjacent to the longitudinal axis of the bone plate.

7. A spinal fixation system as recited in claim 1, wherein each flexure slot terminates at a location on the longitudinal axis of the bone plate.

8. A spinal fixation system as recited in claim 1, wherein each flexure slot terminates in a rounded surface.

9. A spinal fixation system as recited in claim 1, wherein each flexure slot has a substantially similar length.

10. A spinal fixation system as recited in claim 1, further comprising a first bone fastener dimensioned and configured to extend through a first bore in the first end portion of the bone plate to secure the bone plate to a first vertebra and a second bone fastener dimensioned and configured to extend through a second bore in the first end portion of the bone plate to secure the bone plate to a second vertebra.

11. A spinal fixation system as recited in claim 10, wherein each bone fastener is secured within the bore of the locking plate by a threaded locking nut.

12. A spinal fixation system as recited in claim 10, wherein each bone fastener is secured within the bore of the locking plate by a compressible locking washer.

13. A spinal fixation system as recited in claim 1, wherein each end portion of the bone plate has a pair of adjacent bores extending therethrough, each for receiving a bone fastener to secure the bone plate to vertebra.

14. A spinal fixation system as recited in claim 1, wherein each bore in the bone plate is countersunk.

15. A spinal fixation system comprising:
    a) an elongated bone plate having a central longitudinal axis and a predetermined thickness, the bone plate defined by opposed first and second end portions, opposed top and bottom surfaces and an outer periphery, the outer periphery of the bone plate defined in part by opposed first and second lateral edges, at least one flexure slot extending inwardly from the first lateral edge of the bone plate, at least one flexure slot extending inwardly from the second lateral edge of the bone plate, the flexure slots terminating at locations spaced from one another, each end portion of the bone plate having at least two bores formed therein, each bore dimensioned and configured to receive a threaded bone fastener; and
    b) a threaded bone fastener adapted for locked engagement within each bore of the bone plate and configured to secure the bone plate to vertebrae.

16. A spinal fixation system as recited in claim 15, wherein each flexure slot extends at an acute angle with respect to the longitudinal axis of the bone plate.

17. A spinal fixation system as recited in claim 15, wherein each flexure slot extends substantially perpendicular to the longitudinal axis of the bone plate.

18. A spinal fixation system as recited in claim 15, wherein a plurality of flexure slots extend inwardly from the first lateral edge of the bone plate, and a plurality of flexure slots extend inwardly from the second lateral edge of the bone plate.

19. A spinal fixation system as recited in claim 15, wherein each flexure slot extends through the thickness of the bone plate from the top surface thereof to the bottom surface thereof and terminates at a location substantially along the longitudinal axis of the bone plate.

20. A spinal fixation system as recited in claim 15, wherein each flexure slot has a substantially similar length and terminates in a rounded surface.

21. A spinal fixation system as recited in claim 15, wherein each flexure slot terminates at a location adjacent to the longitudinal axis of the bone plate.

22. A spinal fixation system as recited in claim 15, wherein each flexure slot terminates at a location on the longitudinal axis of the bone plate.

23. A spinal fixation system as recited in claim 15, wherein each bone fastener is secured within the bore of the locking plate by at least one of a threaded locking nut and a compressible locking washer.

24. A spinal fixation plate comprising: an elongated plate body having a central longitudinal axis, opposed top and bottom surfaces and an outer periphery, the outer periphery of the plate body defined in part by opposed first and second lateral edges, a plurality of flexure slots extending inwardly from the first lateral edge perpendicular to the longitudinal axis of the plate body, a plurality of flexure slots extending inwardly from the second lateral edge perpendicular to the longitudinal axis of the plate body, the flexure slots terminating at locations axially spaced from one another relative to the longitudinal axis of the plate body.

25. A spinal fixation system as recited in claim 23, wherein each flexure slot has a substantially similar length with respect to the longitudinal axis of the bone plate.

26. A spinal fixation system as recited in claim 23, wherein the bone plate has flexure slots of different length with respect to the longitudinal axis of the bone plate.

27. A spinal fixation system as recited in claim 23, wherein each flexure slot terminates in a rounded surface configured to reduce stress concentrations.

* * * * *